United States Patent [19]

Falcial et al.

[11] Patent Number: 4,976,265
[45] Date of Patent: Dec. 11, 1990

[54] METHOD OF DETECTING ENTEROGASTRIC REFLUX

[75] Inventors: Riccardo Falcial; Annamaria V. Scheggi; Francesco Baldini; Paolo Bechi, all of Florence, Italy

[73] Assignee: Consiglio Nazionale delle Richerche, Rome, Italy

[21] Appl. No.: 287,480

[22] Filed: Dec. 20, 1988

[30] Foreign Application Priority Data

Dec. 23, 1987 [IT] Italy .................................. 9584 A/87

[51] Int. Cl.$^5$ .............................................. A61N 5/06
[52] U.S. Cl. ..................................... 128/634; 128/665
[58] Field of Search ............................... 128/632–634, 128/664–665, 898; 604/20; 356/256

[56] References Cited

U.S. PATENT DOCUMENTS 4,567,882  2/1986  Heller .................................. 128/665

FOREIGN PATENT DOCUMENTS 109826  5/1984  European Pat. Off. ............ 128/665

Primary Examiner—Lee S. Cohen
Assistant Examiner—David Shay
Attorney, Agent, or Firm—McGlew & Tuttle

[57] ABSTRACT

According to the method of detecting enterogastric reflux, the absorption of electromagnetic radiation by the gastric juice is measured at at least two wavelengths of the said radiation, one of said wavelengths corresponding to an absorption peak of a component of the bile and the other having a wavelength value at which the absorption is unaffected by the concentration of bile.

7 Claims, 4 Drawing Sheets

METHOD OF DETECTING ENTEROGASTRIC REFLUX

FIELD AND BACKGROUND OF THE INVENTION

The invention relates to a method of detecting enterogastric reflux and to apparatus for implementing said method.

Enterogastric reflux, i.e. the reflux of bile from the duodenum into the stomach, is an important phenomenon in gastroenterology. It has, in fact, been found that the presence of bile in the gastric juice can have a harmful effect on the esophageal mucosa. Furthermore, although it has not yet been shown that the said reflux has a manifest effect on the nonoperated stomach, it has been demonstrated that erythema and foveolate hyperplasia of the gastric mucosa correlate with enterogastric reflux after partial gastrectomy. In addition, enterogastric reflux can be responsible for a number of dyspeptic syndromes of uncertain classification. It is therefore necessary to perform in-vivo tests to determine whether bile is present in the gastric juice of the patient.

At present, the most widely used method of detecting enterogastric reflux is based on measurements of the acidity of the gastric juice. It is well-known, in fact, that gastric juice—under normal conditions—has a pH value of between 2 and 3, whereas the pH of the bile is approximately 7. A reflux of bile into the stomach therefore raises the pH of the gastric juice since it reduces its acidity. In the current method, therefore, a glass electrode capable of detecting the concentration of hydrogen ions in the gastric juice is introduced into the stomach of the patient for the purpose of effecting continuous monitoring—over a period of up to a whole day—of the acidity of the gastric juice, thereby obtaining indirect evidence of the presence of enterogastric reflux. This method has numerous limitations and disadvantages.

The need to apply a voltage, albeit a very small one, to the probe necessitates the use of expensive equipment to ensure that specific safety standards are met.

In addition, the findings are not reliable: if the sensitive part of the electrode comes to rest on the internal mucosa of the stomach, this will be sufficient to give a false indication of reflux. This is because the mucosa is kept at a pH of approximately 7, i.e. in a neutral condition. If the probe touches these tissues, it will automatically register a rise in pH, which may be erroneously interpreted as a sign of enterogastric reflux, whereas such reflux may not have taken place.

Furthermore, under some conditions (partial gastrectomy, atrophic gastritis, etc.) in which the pH of the gastric juice is almost neutral, enterogastric reflux may not be detected by monitoring the pH value.

As mentioned above, the monitoring may last for many hours. During the period of time that the probe is in the patient's stomach it is necessary to give the patient food. The ingestion of food brings about changes in the acidity of the gastric juices, making it necessary to disregard the measurements taken over a specific period of time (approximately one and a half hours) after the food is consumed.

The method currently in use also does not permit the reflux of bile into the esophagus to be detected, since the pH value in the esophagus is close to 7 and the reflux of bile therefore has no effect on this pH value.

Finally, since the normal pH values of the gastric juice and the bile do not remain perfectly constant, the current method of detection does not permit quantitative, but only qualitative measurement of the reflux.

SUMMARY AND OBJECT OF THE INVENTION

The object of the invention is a method of detecting enterogastric reflux that does not have the limitations and disadvantages mentioned above.

Substantially, the method of detecting enterogastric reflux according to the invention is characterized in that it measures the degree of absorption of electromagnetic radiation by the gastric juice at at least two wavelengths of the said radiation, one of said wavelengths corresponding to an absorption peak of a component of the bile and the other having a value at which absorption is unaffected by the concentration of bile.

Advantageously, the first of said measurements is taken at a wavelength of approximately 460 nm, at the absorption peak of bilirubin, while the second of the said measurements can be taken at a wavelength of approximately 600 nm.

In practice, electromagnetic radiation at these two wavelengths is directed into the stomach of a patient, said radiation is detected—after passing through a sample of gastric juice—at said two wavelength values, and the intensity values measured are compared to determine the concentration of bile in the sample investigated.

To permit subsequent amplification of the signal, the radiation can be modulated.

In one practical embodiment, the radiation detected at each of said two wavelengths is converted into an electrical signal, said signal is amplified, filtered and rectified, and the two signals obtained are compared to obtain a signal proportional to the concentration of bile in the gastric juice.

The electrical signals corresponding to the two wavelengths may be converted into digital signals and fed into a computer.

The invention also relates to apparatus for implementing the method of detecting enterogastric reflux, which consists of a sensor comprising a capillary tube made of material resistant to the action of gastric juice, into one end of which are introduced and fixed respectively the terminal end of one or more optical fibers for the transmission and detection of the radiation; the opposite end of said capillary tube is sealed by a mirror-wall, and between this mirror-wall and said optical fiber(s) are provided apertures for the passage of the juice to be examined.

Said apparatus can also include at least one radiation source; at least one optical fiber to convey said radiation to a sensor to be introduced into the stomach of the patient; at least one optical fiber to receive the radiation after it has passed through the sample of gastric juice and convey it to organs of detection; and, connected to said organs of detection, devices for converting and processing the signal received.

In one possible embodiment, the said radiation source is a halogen lamp; two optical fibers can be provided to collect the radiation after it has passed through the sample of gastric juice, while at the output of said two optic fibers are provided filters for preset wavelengths.

Advantageously, the first of said filters is transparent to radiation of approximately 460 nm and the second filter is transparent to radiation of approximately 600 nm.

In practice, said halogen lamp is connected to a modulating device and said organs of detection comprise in combination, for each wavelength used: a photodiode, an amplifier, a circuit for filtering and a circuit for rectifying the signal. An analog-digital converter may also be provided, at the input of which are fed the signals from the rectifiers and the output of which is transmitted to a digital computer.

In a modified embodiment, the source can comprise two light-emitting diodes, which emit radiation at two preset wavelengths; said radiation is conveyed to said sensor by means of two optic fibers. In practice, the first of said diodes emits light radiation with a peak at the wavelength of 460 nm, and the second diode emits at a wavelength at which the absorption is unaffected by the concentration of bile in the sample of gastric juice under investigation.

To reduce the dimensions of the sensor, one can provide for the optic fibers from the light source to converge in a directional coupler, from which a single optic fiber conveys the radiation to the sensor! In addition, the optic fiber(s) that collect the radiation after it has passed through the sample of gastric juice come from said directional coupler, a single optic fiber conveying the radiation from said coupler to the said sensor and the radiation modulated by the gastric juice from said sensor to said coupler.

A better understanding of the invention will be achieved by following the description and the attached drawings, which show possible, nonlimiting embodiments of the said invention. In the drawings.

DETAILED DESCRIPTION OF THE PREFERRED EMBODIMENTS

Figure 1:
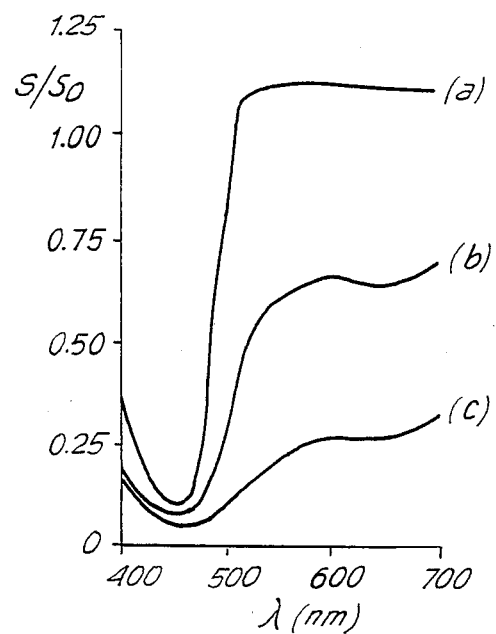
FIG. 1 shows a diagram giving the results of spectrophotometric measurements on human bile.

FIG. 1 shows the transmission spectra, standardized in relation to the transmission value of air (indicated by So), of, respectively:

a solution of bilirubin in chloroform (curve a);
human bile (curve b); and
gastric juice of a patient suffering from enterogastric reflux (curve c).

As can be seen from the diagram, bilirubin, the pigment present in the bile, has an absorption peak at a wavelength of 460 nm, as shown by a trough in the curve (a). The same absorption peak occurs, as is to be expected, in the transmission measurements performed on the bile, though these show a further transmission trough at a wavelength of approximately 650 nm, which corresponds to the absorption peak of another pigment present in bile (biliverdin). As expected, the transmission measurements taken in a sample of gastric juice from a patient suffering from enterogastric reflux (curve c) also show a transmission trough at a wavelength of 460 nm.

The method according to the invention exploits the results of the spectrophotometric measurements reported above and is based on the concept of detecting the presence of bile in the gastric juice by measuring the transmission of the said juice.

Figure 2:
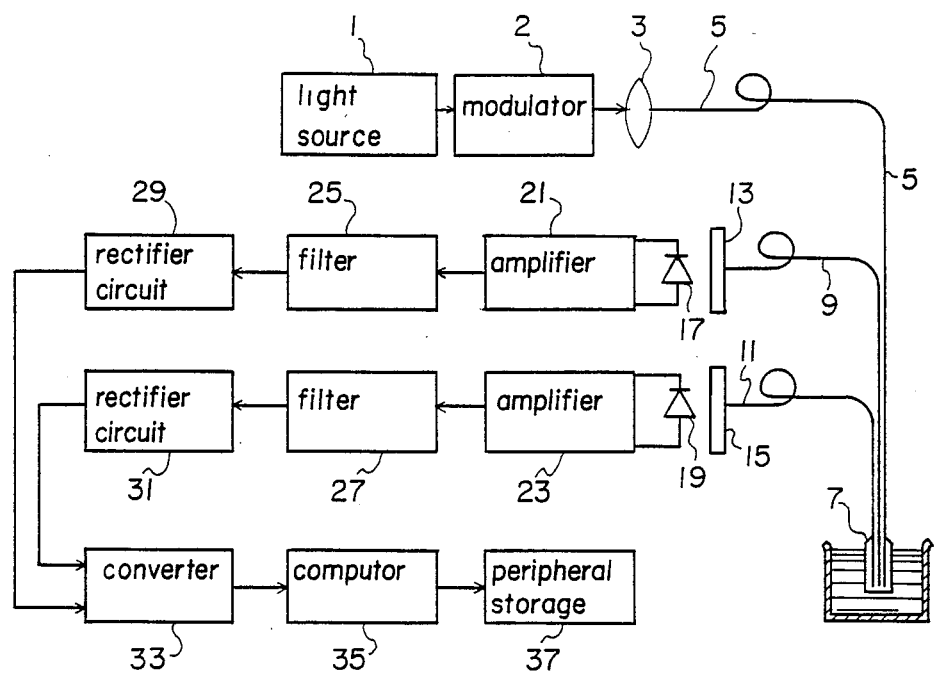
FIG. 2 shows a diagrammatic representation of apparatus for the implementation of the method of detection according to the invention.

FIG. 2 shows a diagram of the functioning of an initial embodiment of apparatus for the implementation of the method according to the invention.

A light source 1, for example a halogen lamp, emits radiation at various wavelengths, including radiation at a wavelength of 460 nm, which corresponds to the absorption peak of bilirubin, and radiation at a wavelength which does not correspond to any peak or trough in the absorption curves, for example approximately 600 nm.

The light beam emitted by the source 1 is conveyed via a lens 3, along an optic fiber 5 to a sensor 7, which is described in greater detail below. In the sensor 7, which is suitable for introduction into the stomach of the patient, the light radiation is modulated by the gastric juice and then collected by two further optic fibers 9 and 11 and transmitted to detecting elements through two band-pass filters 13 and 15 respectively, one set at a wavelength of 460 nm, corresponding to the absorption peak of bilirubin, and the other at a wavelength where the absorption is unaffected by the concentration of bilirubin (for example, 600 nm).

The filtered radiation is detected by two photodiodes 17,19 and converted into corresponding electrical signals which can be subjected to the subsequent processing. To enable the signal detected to be amplified, the light from the source 1 is modulated by a modulator 2 (known as a "chopper") before it is introduced into the optic fiber 5. The signal that reaches the photodiodes 17,19 and the corresponding electrical signal are consequently of an alternating type, for example in the form of a square wave. The signals emitted by the photodiodes 17,19 are amplified by corresponding amplifiers 21,23, suitably filtered by filters 25 and 27 and then converted into direct signals in rectifier circuits 29,31.

At the output of the rectifiers 29,31 there are therefore two direct current signals whose intensity is proportional to the absorption of the gastric juice–in which the sensor 7 is immersed–at the wavelengths at which the band-pass filters 17 and 19 are set. These two signals can be compared and the resulting signal converted, in an analog-digital converter 33, into a digital signal that can be fed into a computer 35 for further computational processing, the plotting of diagrams with the aid of an appropriate peripheral 37, storage in memory and other operations.

Figure 3:
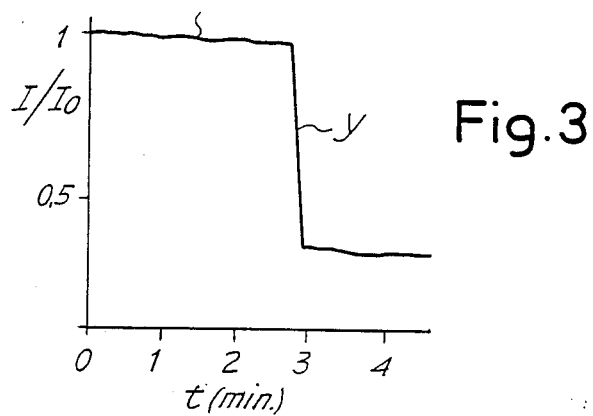
FIG. 3 shows a diagrammatic representation of a response curve obtained with apparatus of the type shown in FIG. 2.

As the ratio of the two measured values is unaffected by any fluctuations in the source, the information supplied at the output of the converter 33 is unaffected by said fluctuations. FIG. 3 shows an example of a diagram that can be obtained with apparatus of the type illustrated in an in-vitro detection test. The ordinate shows the ratio, $I/I_o$, of the intensity of the radiation collected by the photodiode 17 to the intensity of the radiation collected by the photodiode 19, while the abscissa shows the time in minutes. If the sample of gastric juice being monitored contains no bile, the ratio $I/I_o$ remains at a value of approximately 1, as shown by the section of curve X. When gastric juice containing bile is added, there is a break Y in the detection curve and the ratio $I/I_o$ falls to values well below unity.

Figure 4:
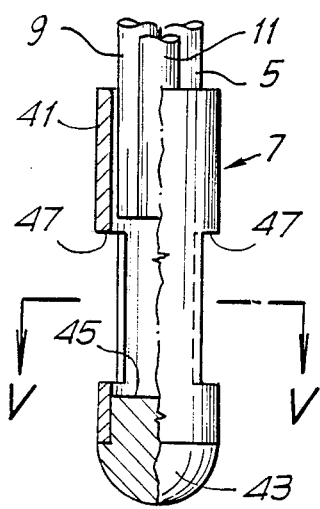
FIG. 4 shows a lateral and partial longitudinal section view of a sensor.
Figure 5:
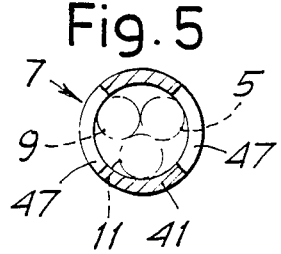
FIG. 5 shows a cross-section according to V—V of FIG. 4.

FIG. 4 shows a possible embodiment of the sensor 7. In this embodiment, the sensor 7 comprises a capillary tube 41 in material resistant to the action of the gastric juice, for example stainless steel, that is approximately 2 cm long and has an external diameter that depends on the diameter of the optic fibers used; for example, if the optic fibers used have an internal nucleus with a diameter of 600 μm, a capillary tube with an external diameter of approximately 2.5 mm can be used. At one end of the capillary tube 41 are fixed the ends of the optic fibers 5,9,11, while the other end is sealed by an element 43 that has a mirror surface 45 facing the ends of the optic fibers. The cylindrical lateral mantle of the capillary tube 41 bears apertures 47 to permit the free penetration of the gastric juice into the sensor 7 between the ends of the optic fibers and the mirror surface 45. In this way, the light radiation emanating from the optic fiber 5 passes through the sample of gastric juice that has penetrated into the capillary tube via the apertures 47, is reflected by the surface 45 and reaches the optic fibers 9 and 11, which convey it to the organs of detection and in particular to the band-pass filters 13,15.

The method and apparatus according to the invention enable monitoring to be performed over prolonged periods of time with minimal discomfort for the patient without the measurements being affected by any food consumption and without the need to introduce voltage-carrying electrical wires into the esophagus and stomach of the patient. The sensor 7 can, in fact, be made smaller than the ordinary glass sensors used to measure the pH of the gastric juice. Furthermore, since it is an optical characteristic (transmission) of a substance present in the bile that is being measured, and the method therefore detects the presence of bilirubin in the gastric juice directly, there can be no errors due to spurious factors that affect an order of magnitude, such as acidity, that correlates only indirectly with the presence of bilirubin. It is therefore possible, for example, to test for enterogastric reflux even during and after the ingestion of food, providing the latter is administered in a liquid form that is sufficiently transparent to the radiation used for the test. The presence of liquid food in the stomach will, in fact, have the effect of causing an overall—and roughly uniform over the entire range of wavelengths of the radiation from the source 1—lowering of the transmission curve, this effect being cancelled out when the ratio of the two values found for the intensity of radiation is worked out.

It is clear, finally, that this method can be used to make not only qualitative but also quantitative measurements of enterogastric reflux; the change in the ratio I/Io is, in fact, proportional to the concentration of bilirubin in the stomach.

The apparatus for implementing the method according to the invention can also include, instead of a halogen lamp, one or more light-emitting diodes. In the embodiment in FIG. 6, for example, the light source comprises two light-emitting diodes (LED) 51,53, controlled by two electronic circuits 55,57. The first of said diodes can emit light radiation with a peak at a wavelength of 460 nm, while the second can emit light radiation at a wavelength of approximately 600 nm or another suitable wavelength. The two radiations are conveyed by two optic fibers 59,61, via a directional coupler 62, to a single optic fiber 63 connected to the sensor 7, from which another optic fiber 65 conveys the radiation collected after it has passed through the sample of gastric juice to organs of detection similar to those described earlier. Said organs comprise a photodiode 67, an amplifier 69, a filter 71, a circuit 73 capable of picking up the two signals emitted by the light-emitting diodes 51,53. Downstream of the said circuit 73 are provided a rectifier 75, an analog-digital converter 77, a computer 79 and any peripherals 81, for example for plotting diagrams. Known methods of data transmission can be used for the emission of the signal by the light-emitting diodes 51,53 and the subsequent detection by the organs 67, 69, 71, 73.

Figure 7:
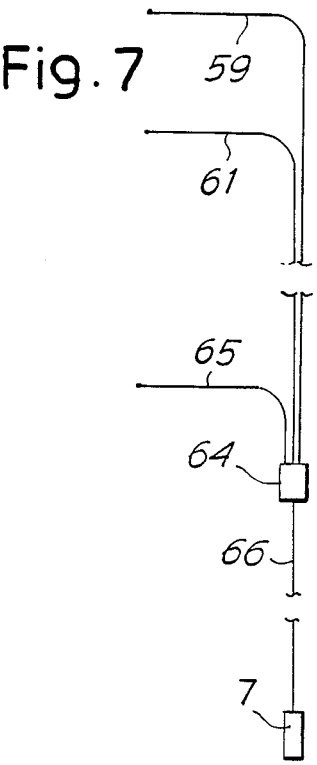
FIG. 7 shows another type of apparatus for implementing the method according to the invention.
Figure 6:
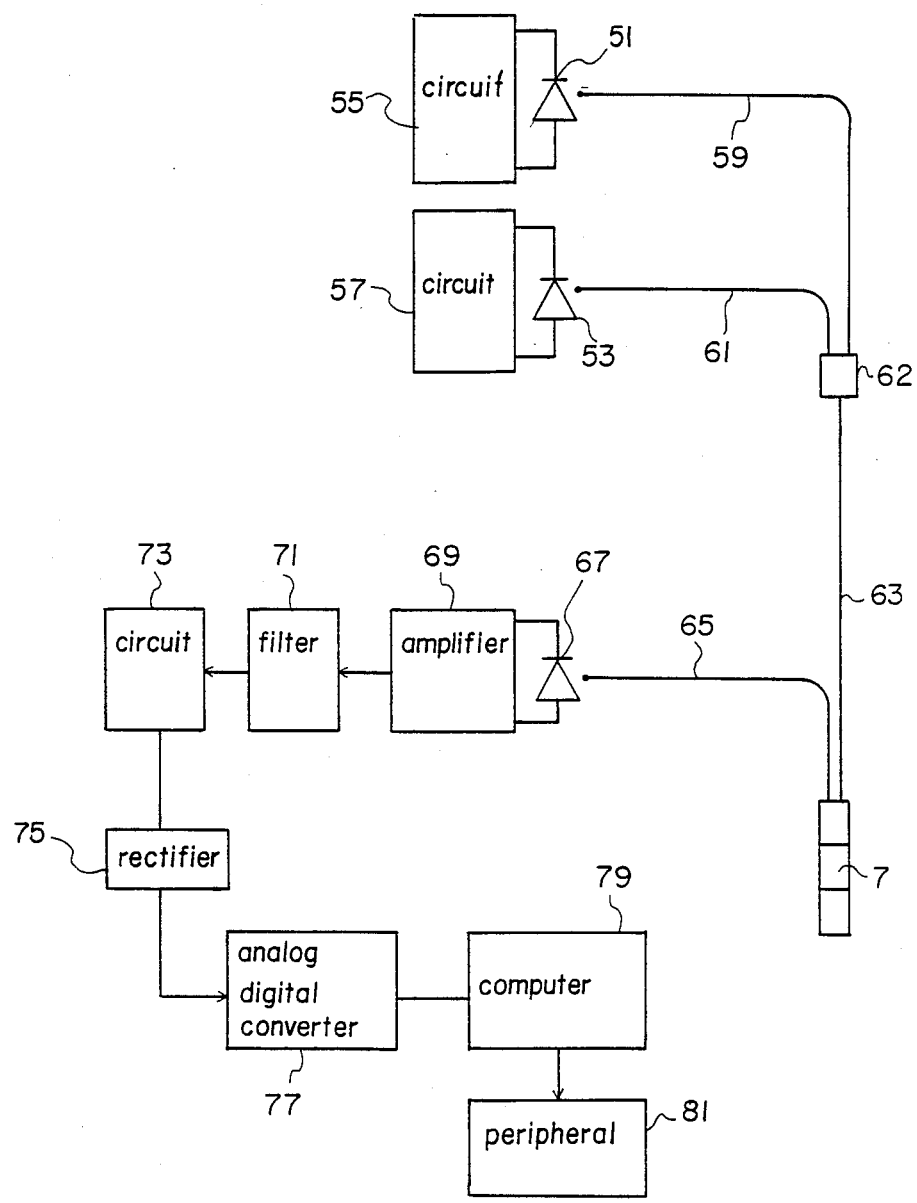
FIG. 6 shows one type of apparatus for implementing the method according to the invention.

FIG. 7 shows a variant of the solution shown in FIG. 6 (relating only to the diagram of the probe) in which both the optic fibers originating from the source and the optic fiber connected to the organs of detection converge in a directional coupler 64. A single optic fiber 66 then connects the coupler 64 to the sensor 7, said fiber serving to convey the radiation in both directions. This enables the dimensions of the sensor 7 to be further reduced, thereby increasing the tolerability to the patient during the monitoring procedure.

The drawing shows only one example, given only as a practical demonstration of the invention; it is possible to vary the forms and dispositions of the said invention without departing from the concept on which the said invention is based.

What is claimed is:

1. A method of detecting enterogastric reflux, comprising the steps of measuring the absorption of electromagnetic radiation by gastric juice of a patient at at least two wavelengths, one of said wavelengths corresponding to an absorption peak of a bile component and another of said wavelengths having a value at which absorption is unaffected by a concentration of said bile determining whether or not there is endogastric reflux based on the measurement of the absorption of the electromagnetic radiation at said wavelengths.

2. The method of detecting enterogastric reflux as claimed in claim 1, wherein a first measurement of said step of measuring is made at a wavelength of approximately 460 nm, which corresponds to the absorption peak of bilirubin.

3. The method of detecting enterogastric reflux as claimed in claim 2, wherein a second measurement of said step of measuring is made at a wavelength of approximately 600 nm.

4. The method of detecting enterogastric reflux as claimed in claim 1, wherein electromagnetic radiation in said two wavelengths is transmitted into the stomach of a patient, wherein said radiation—after passing through a sample of gastric juice—is detected at the said two wavelength values, and wherein the intensity values found are compared to obtain a measurement of a concentration of bile in the sample examined.

5. The method of detecting enterogastric reflux as claimed in claim 1, wherein the said radiation is modulated.

6. The method of detecting enterogastric reflux as claimed in claim 1, wherein the radiation detected at each of said two wavelengths is converted into an electrical signal, said signal is amplified, filtered and rectified, and the two signals obtained are compared to obtain a signal proportional to a concentration of bile in the gastric juice.

7. The method of detection as claimed in claim 6, wherein the electrical signals corresponding to the two wavelengths are converted into digital signals and fed into a computer.

* * * * *